United States Patent

Chern et al.

(10) Patent No.: US 6,815,444 B2
(45) Date of Patent: Nov. 9, 2004

(54) ANTI-ENTEROVIRUS COMPOUNDS

(75) Inventors: Jyh-Haur Chern, Taipei (TW); Kak-Shan Shia, Taipei (TW); Shin-Ru Shih, Tao-Yuan (CN); Tsu-An Hsu, Taipei (TW); Chia-Liang Tai, Taipei (TW)

(73) Assignee: National Health Research Institutes, Taipei (TW)

( * ) Notice: Subject to any disclaimer, the term of this patent is extended or adjusted under 35 U.S.C. 154(b) by 0 days.

(21) Appl. No.: 10/444,747

(22) Filed: May 23, 2003

(65) Prior Publication Data

US 2004/0204400 A1 Oct. 14, 2004

Related U.S. Application Data

(60) Provisional application No. 60/382,925, filed on May 24, 2002.

(51) Int. Cl.$^7$ .................... C07D 487/04; A61K 31/519
(52) U.S. Cl. .................. 514/252.16; 544/262
(58) Field of Search ...................... 514/252.16; 544/262

(56) References Cited

U.S. PATENT DOCUMENTS 6,218,397 B1  4/2001  Chen ...................... 514/258

OTHER PUBLICATIONS

Dhainaut et al., "New Purines and Purine Analogs as Modulators of Multidrug Resistance", J. Med. Chem. 39:4099–4108, 1996.

He et al., "4-(1,3-Dimethoxyprop-2-ylamino)-2.7-dimethyl-8-(2,4-Dichlorophenyl)-Pyrazolo[1,5-a]-1,3,5-Triazine: A Potent, Orally Bioavailable $CFR_1$ Receptor Antagonist", M. Med. Chem. 43:449–456, 2000.

Gilliagn et al., The Discovery of 4-(3-Pentylamino)-2, 7-Dimethyl-8-(2-Methyl-4-Methoxyphenyl)-Pyrazolo-[1,5-α]-Pyrimidine: A Corticotropin-Releasing Factor ($hCFR_1$) Antagonist), Bioorganic & Medicinal Chemistry 8:181–189, 2000.

Pevear et al., "Activity of Pleconaril Against Enteroviruses", Antimicrobial Agents and Chemotherapy 43:2109–2115, 1999.

Shia et al., "Design, Synthesis, and Structure–Activity Relationship of Pyridyl Imidazolidinones: A Novel Class of Potent and Selective Human Enterovirus 71 Inhibitors", Journal of Medicinal Chemistry 45:1644–1655, 2002.

Primary Examiner—Bruck Kifle
(74) Attorney, Agent, or Firm—Fish & Richardson P.C.

(57) ABSTRACT

This invention features, among others, a pyrazolopyrimidine compound of formula (A):

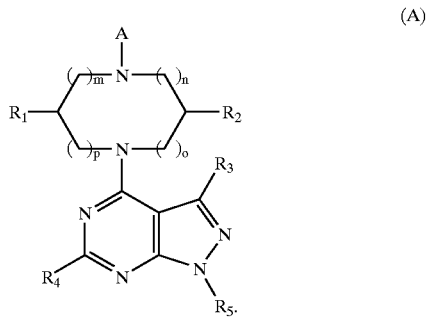

A is $(CH_2)_q$—$CHR^aR^b$; each of $R_1$ and $R_2$, independently, is hydrogen, halogen, cyano, nitro, or alkyl; or $R_1$ and $R_2$ taken together is $(CH_2)_r$; each of $R_3$ and $R_4$, independently, is hydrogen, halogen, cyano, nitro, or alkyl; each of $R_5$, $R^a$, and $R^b$, independently, is aryl, aralkyl, or heteroaryl, optionally substituted with halogen, cyano, nitro, alkyl, aryl, aralkyl, heteroaryl, OR, O(O)CR, C(O)R, C(O)OR, C(O)NRR', SR, S(O)R, S(O)OR, NRR', NR(O)CR', NRC(O)OR', or NRC(O)NR'R"; each of m, n, o, p, and r, independently, is 0 or 1, and q is 0, 1, or 2; in which each of R, R', and R", independently, is hydrogen or alkyl, provided that the sum of m, n, o, and p is 1, 2, 3, or 4.

41 Claims, No Drawings

ANTI-ENTEROVIRUS COMPOUNDS

CROSS REFERENCE TO RELATED APPLICATION

Pursuant to 35 USC § 119(e), this application claims the benefit of prior U.S. Provisional Application Ser. No. 60/382,925, filed May 24, 2002.

BACKGROUND

Enteroviruses belong to the family Picornaviridae. They include about 70 human serotypes, e.g., polioviruses, coxsackieviruses A (COX A1–24), coxsackieviruses B (COX B1–6), echoviruses 1–31, enteroviruses (EV68–71), and enterovirus 72 (hepatitis A).

Genomic sequences among various enteroviruses are well conserved. The virion of an enterovirus consists of a simple virus capsid and a single strand of RNA. The viral genome encodes a polyprotein that is proteolytically processed by host and viral proteases into 11 different mature proteins which are encoded in the following order: $NH_2$-VP4-VP2-VP3-VP1-2A-2B-2C-3A-3B-3C-3D-$CO_2H$. *Virology* Ed. Field, B. N. 1985. The single-stranded RNA is replicated by viral RNA polymerase. See, e.g., Holland et al. (1982) *Science* 215: 1576–1585; Ward et al. (1988) *J. Virol.* 62: 558–562; and La Torre et al. (1990) *J. Virol.* 64: 664–671.

Enteroviruses primarily enter the body through the alimentary canal. They replicate in the cell lining of the alimentary canal before spreading throughout the body via the blood circulation. Clinical syndromes of enteroviral infections are generally mild. Occasionally, enteroviruses cause serious diseases such as paralytic poliomyelitis, meningitis, or myocarditis.

There is a need to develop compounds which are effective in treating infection by enteroviruses.

SUMMARY

The present invention is based on the identification of new compounds for use as a therapeutic agent to treat enteroviral infection.

In one aspect, this invention encompasses pyrazolopyrimidine compounds of formula (A):

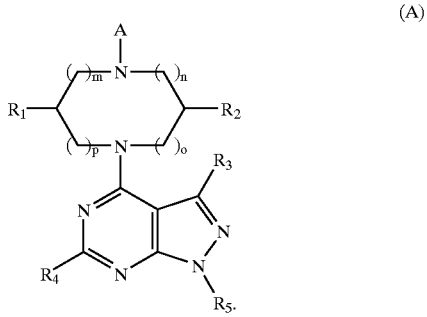

(A)

A is $(CH_2)_q$—$CHR^aR^b$; each of $R_1$ and $R_2$, independently, is hydrogen, halogen, cyano, nitro, or alkyl; or $R_1$ and $R_2$ taken together is $(CH_2)_r$; each of $R_3$ and $R_4$, independently, is hydrogen, halogen, cyano, nitro, or alkyl; each of $R_5$, $R^a$, and $R^b$, independently, is aryl, aralkyl, or heteroaryl, optionally substituted with halogen, cyano, nitro, alkyl, aryl, aralkyl, heteroaryl, OR, O(O)CR, C(O)R, C(O)OR, C(O) NRR', SR, S(O)R, S(O)OR, NRR', NR(O)CR', NRC(O)OR', or NRC(O)NR'R''; each of m, n, o, p, and r, independently, is 0 or 1, and q is 0, 1, or 2; in which each of R, R', and R'', independently, is hydrogen or alkyl, provided that the sum of m, n, o, and p is 1, 2, 3, or 4. Note that the left atom shown in any substituted group described above is closest to the pyrazolopyrimidine ring. Also note that if there are more than one R-containing substituted groups in a pyrazolopyrimidine compound of this invention, the Rs can be the same or different. The same rule applies to other similar situation.

Referring to formula (A), a subset of the pyrazolopyrimidine compounds of this invention are those in which each of $R_1$ and $R_2$ is hydrogen. In some embodiments, the sum of m and p is 1 and the sum of n and o is also 1. In other embodiments, the sum of m and p is 1, and the sum of n and o is 2. In this subset of pyrazolopyrimidine compounds, q can be 0; each of $R^a$ and $R^b$, independently, can be aryl or heteroaryl; $R_5$ can be phenyl, and each of $R_3$ and $R_4$ can be hydrogen.

Another subset of the pyrazolopyrimidine compounds of this invention are those in which $R_1$ and $R_2$ taken together is $(CH_2)_r$, and r is 1. In these embodiments, the sum of m and p can be 1 and the sum of n and o can also be 1; q can be 0; each of $R^a$ and $R^b$, independently, can be aryl; $R_5$ can be aryl (e.g., phenyl); and each of $R_3$ and $R_4$ can be hydrogen.

In another aspect, this invention encompasses pyrazolopyrimidine compounds of formula (A), wherein A is $(CH_2)_q$—$R^a$; each of $R_1$ and $R_2$, independently is hydrogen, halogen, cyano, nitro, or alkyl; or $R_1$ and $R_2$ taken together is $(CH_2)_r$; each of $R_3$ and $R_4$, independently, is hydrogen, halogen, cyano, nitro, or alkyl; $R_5$ is aryl, aralkyl, or heteroaryl, optionally substituted with halogen, cyano, nitro, alkyl, aryl, aralkyl, heteroaryl, OR, O(O)CR, C(O)R, C(O) OR, C(O)NRR', SR, S(O)R, S(O)OR, NRR', NR(O)CR', NRC(O)OR', or NRC(O)NR'R''; $R^a$ is aryl, aralkyl, or heteroaryl, optionally substituted with halogen, cyano, nitro, alkyl, aryl, aralkyl, heteroaryl, OR, O(O)CR, C(O)R, C(O) OR, C(O)NRR', SR, S(O)R, S(O)OR, NRR', NR(O)CR', NRC(O)OR', or NRC(O)NR'R''; each of m, n, o, p, and r, independently, is 0 or 1; and q is 1; in which each of R, R', and R'', independently, is hydrogen or alkyl, provided that the sum of m, n, o, and p is 1, 2, 3, or 4.

In these compounds, $R^a$ can be heteroaryl (e.g., thienyl), $R_5$ can be aryl (e.g., phenyl), and each of $R_1$ and $R_2$ can be hydrogen. In some embodiments, the sum of m and p is 1 and the sum of n and o is also 1, $R_5$ is phenyl, and each of $R_3$ and $R_4$ is hydrogen.

In a further aspect, this invention encompasses pyrazolopyrimidine compounds of formula (A), wherein A is $(CH_2)_q$—$R^a$; each of $R_1$ and $R_2$, independently, is hydrogen, halogen, cyano, nitro, or alkyl; or $R_1$ and $R_2$ taken together is $(CH_2)_r$; each of $R_3$ and $R_4$, independently, is hydrogen, halogen, cyano, nitro, or alkyl; each of $R_5$ and $R^a$, independently, is aryl, aralkyl, or heteroaryl, optionally substituted with halogen, cyano, nitro, alkyl, aryl, aralkyl, heteroaryl, OR, O(O)CR, C(O)R, C(O)OR, C(O)NRR', SR, S(O)R, S(O)OR, NRR', NR(O)CR', NRC(O)OR', or NRC (O)NR'R''; each of m, n, o, p, and r, independently, is 0 or 1; and q is 0 and 2; in which each of R, R', and R'', independently, is hydrogen or alkyl, provided that the sum of m, n, o, and p is 1, 2, 3, or 4.

In these compounds, q can be 0, $R^a$ can be aralkyl (e.g., fluorenyl), $R_5$ can be aryl (e.g., phenyl), and each of $R_1$ and $R_2$ can be hydrogen. In some embodiments, the sum of m and p is 1 and the sum of n and o is also 1, $R_5$ is phenyl, and each of $R_3$ and $R_4$ is hydrogen.

This invention also features a method for treating infection by enteroviruses. The method includes administering to a subject in need thereof an effective amount of a compound of formula (A), wherein A is $(CH_2)_q$—$CHR^aR^b$ or $(CH_2)_q$—$R^a$; each of $R_1$ and $R_2$, independently, is hydrogen, halogen, cyano, nitro, or alkyl; or $R_1$ and $R_2$ taken together is $(CH_2)_n$; each of $R_3$ and $R_4$, independently, is hydrogen, halogen, cyano, nitro, or alkyl; each of $R_5$, $R^a$, and $R^b$, independently, is aryl, aralkyl, or heteroaryl, optionally substituted with halogen, cyano, nitro, alkyl, aryl, aralkyl, heteroaryl, OR, O(O)CR, C(O)R, C(O)OR, C(O)NRR', SR, S(O)R, S(O)OR, NRR', NR(O)CR', NRC(O)OR', or NRC(O)NR'R"; each of m, n, o, p, and r, independently, is 0 or 1; and q is 0, 1, or 2; in which each of R, R', and R", independently, is hydrogen or alkyl, provided that the sum of m, n, o, and p is 1, 2, 3, or 4.

Alkyl, aralkyl, aryl, or heteroaryl herein refers to both substituted and unsubstituted moieties. The term "substituted," in turn, refers to one or more substituents (which may be the same or different), each replacing a hydrogen atom. The substitutents may be the same or different from those described above. Examples of substituents include, but are not limited to, halogen, hydroxyl, amino, alkylamino, arylamino, dialkylamino, diarylamino, cyano, nitro, mercapto, carbonyl, carbamido, carbamoyl, carboxyl, thioureido, thiocyanato, sulfonamido, alkyl, alkenyl, alkoxy, aryl, heteroaryl, cycloalkyl, and heterocycloalkyl, wherein alkyl, alkenyl, alkoxy, aryl, heteroaryl, cycloalkyl, and heterocycloalkyl, are optionally substituted with alkyl, aryl, heteroaryl, halogen, hydroxyl, amino, mercapto, cyano, or nitro. The term "alkyl" refers to a linear or branched, saturated or unsaturated $C_1$–$C_6$ hydrocarbon moiety. The term "alkoxy" refers to a linear or branched, saturated or unsaturated, non-aromatic $C_1$–$C_{10}$ moiety containing an oxygen radical, such as —$OCH_3$ or —$OCH=C_2H_5$. The term "cycloalkyl" refers to a saturated or unsaturated, non-aromatic $C_3$–$C_{10}$ cyclic hydrocarbon moiety. The term "heterocycloalkyl" refers to a saturated or unsaturated, non-aromatic $C_3$–$C_{10}$ cyclic moiety having at least one ring heteroatom, such as O, N, and S. The term "aralkyl" refers to a moiety in which an alkyl hydrogen atom is replaced by an aryl or heteroaryl group. Examples of aralkyl moieties include, but are not limited to, fluorenyl, carbazolyl, 9,10-dihydroanthracenyl, acridanyl, dibenzosuberanyl, iminodibenzyl, and dibenzosuberenyl. The term "aryl" refers to a hydrocarbon ring system having at least one aromatic ring. Examples of aryl moieties include, but are not limited to, phenyl, naphthyl, anthracenyl, perylenyl, and pyrenyl. The term "heteroaryl" refers to a hydrocarbon ring system having at least one aromatic ring that contains at least one heteroatom such as O, N, or S. Examples of heteroaryl moieties include, but are not limited to, pyridinyl, carbazolyl, and indolyl.

The pyrazolopyrimidine compounds described above include the compounds themselves, as well as their salts and their prodrugs, if applicable. Such salts, for example, can be formed by interaction between a negatively charged substituent (e.g., carboxylate) on a pyrazolopyrimidine compound and a cation. Suitable cations include, but are not limited to, sodium ion, potassium ion, magnesium ion, calcium ion, and an ammonium cation such as teteramethylammonium ion. Likewise, a positively charged substituent (e.g., amino) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing pyrazolopyrimidine compounds described above. In addition, some of the pyrazolopyrimidine compounds have one or more asymmetric centers. Such compounds can occur as racemates, racemic mixtures, single enantiomers, individual diastereomers, diastereomeric mixtures.

Also within the scope of this invention is a composition containing one or more of the pyrazolopyrimidine compounds described above for use in treating infection by enterovirus, and the use of such a composition for the manufacture of a medicament for the just-described use.

As used herein, the term "treating infection" refers to use of one or more pyrazolopyrimidine compounds for preventing or treating infection by enterovirus, or other disease states secondary to enteroviral infection.

Shown below are the structures of exemplary pyrazolopyrimidine compounds, i.e., compounds 1–42:

Compound 1

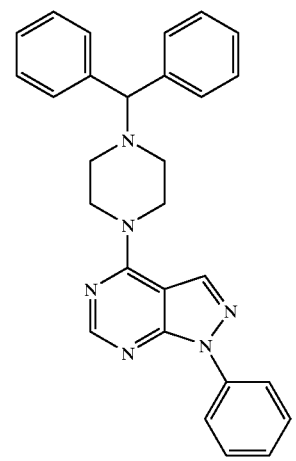

Compound 2

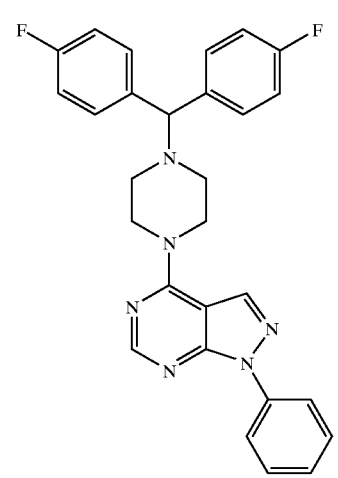

Compound 3
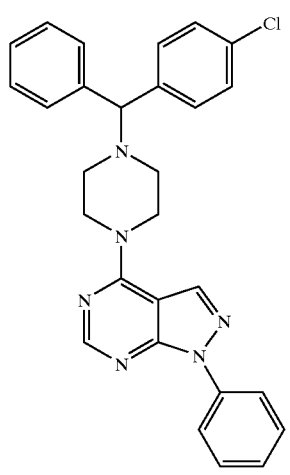
Compound 4
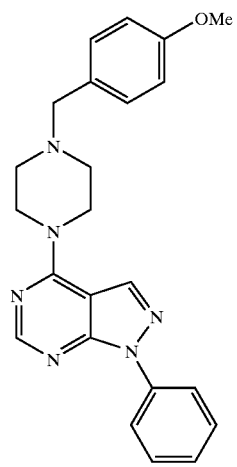
Compound 5
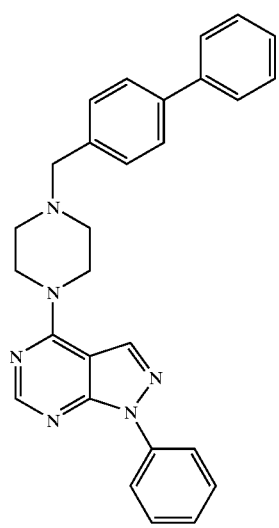
Compound 6
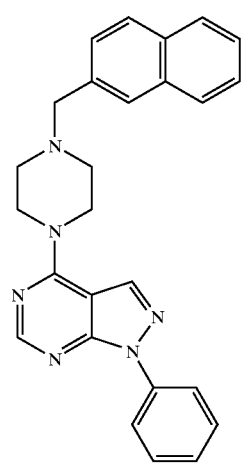
Compound 7
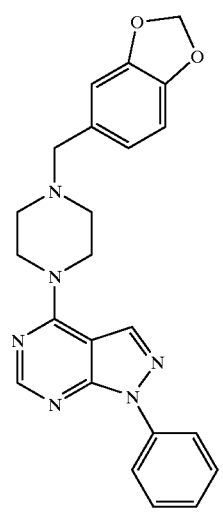
Compound 8
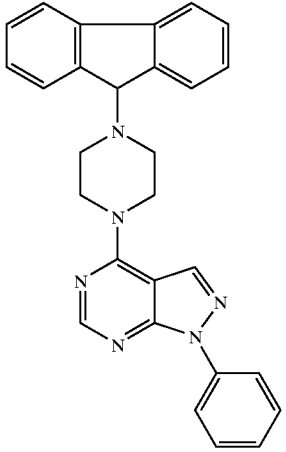

Compound 9
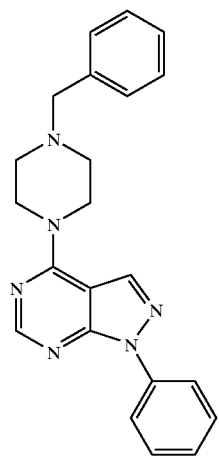
Compound 10
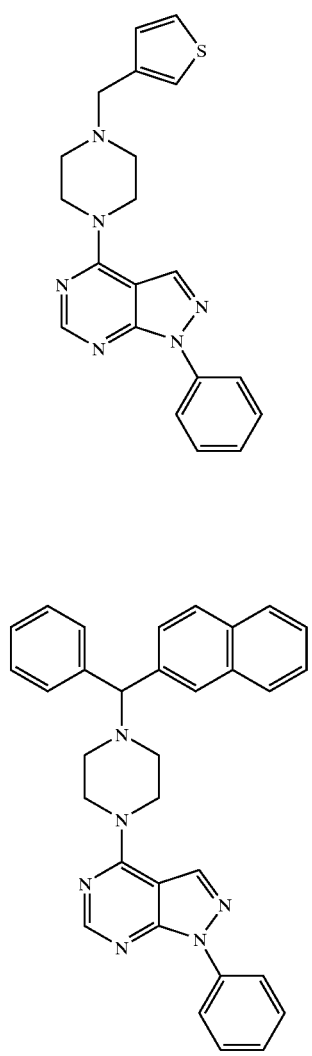
Compound 11
Compound 12
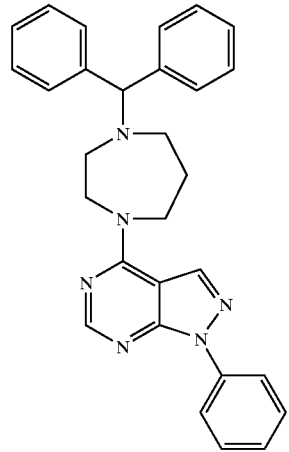
Compound 13
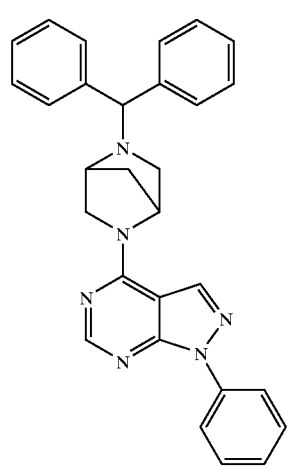
Compound 14
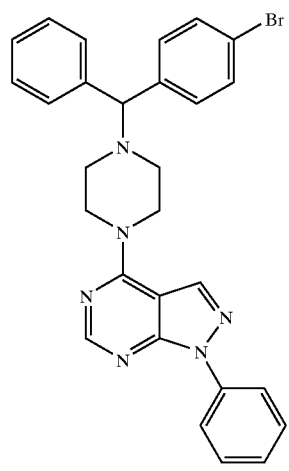

-continued
Compound 15
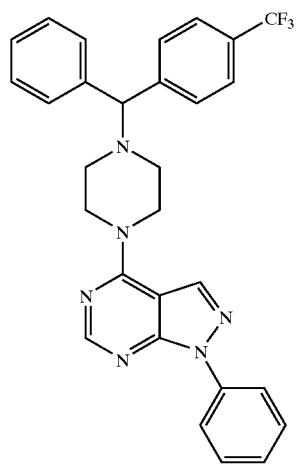
Compound 16
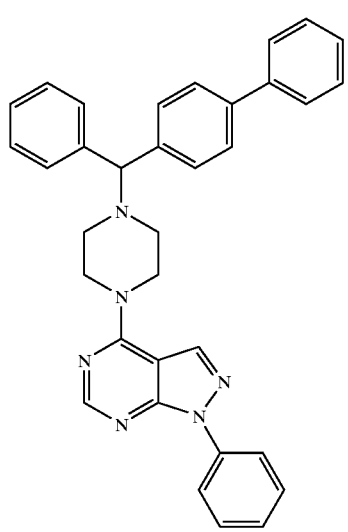
Compound 17
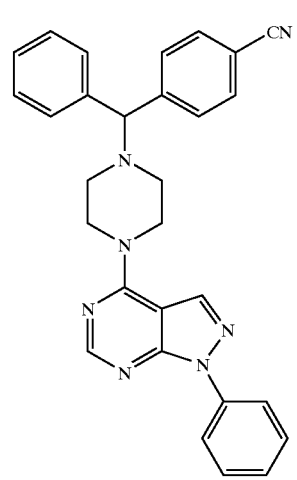
-continued
Compound 18
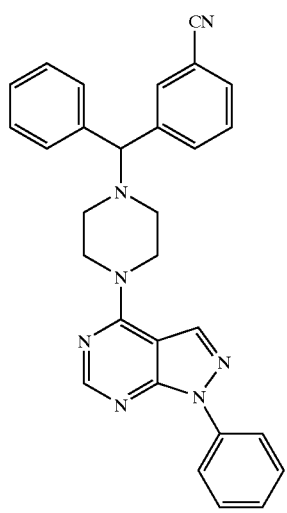
Compound 19
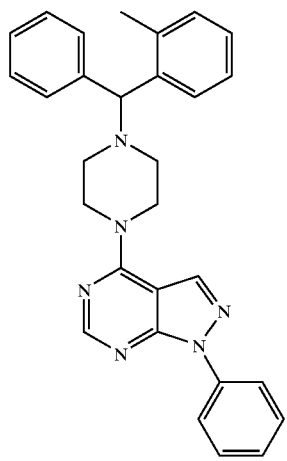
Compound 20
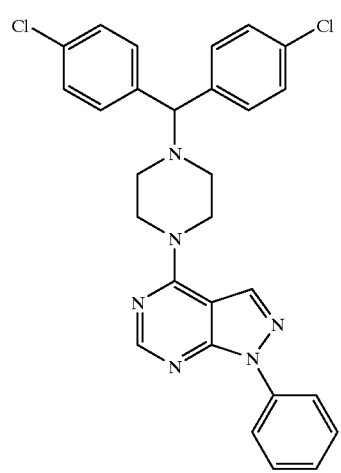

Compound 21
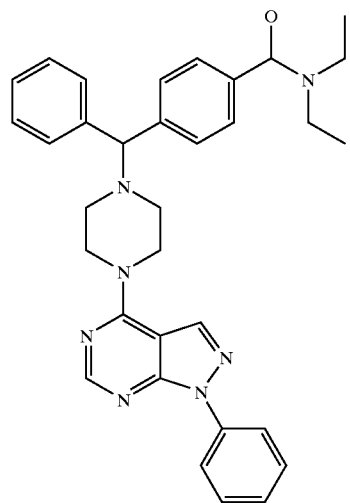
Compound 22
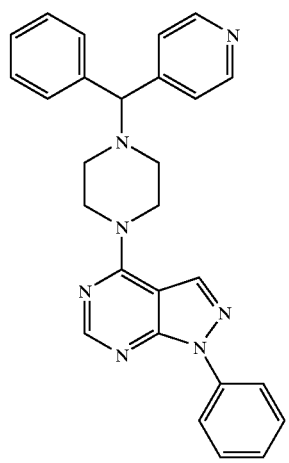
Compound 23
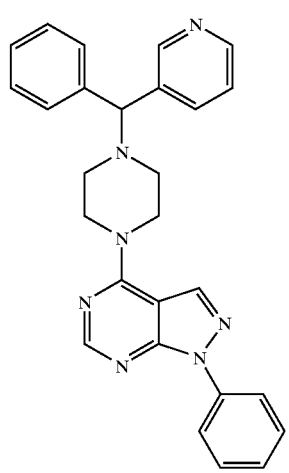
Compound 24
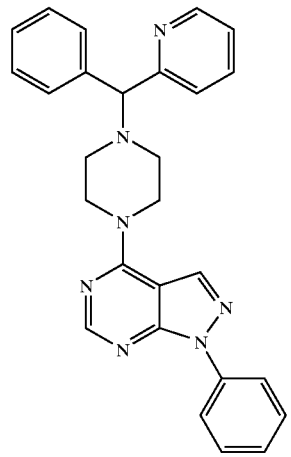
Compound 25
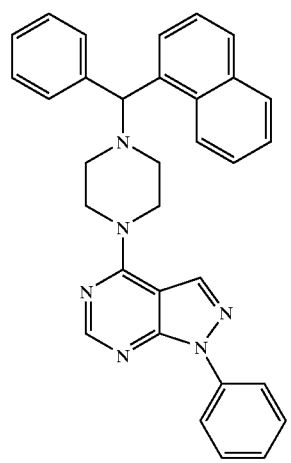
Compound 26
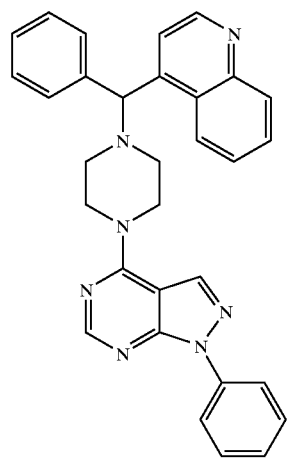

Compound 27
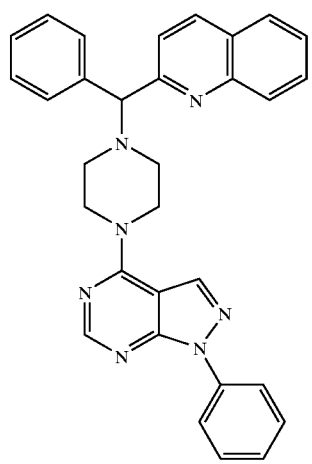
Compound 28
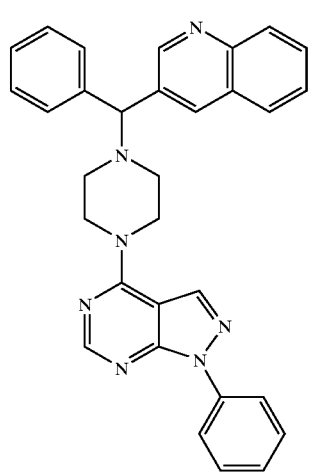
Compound 29
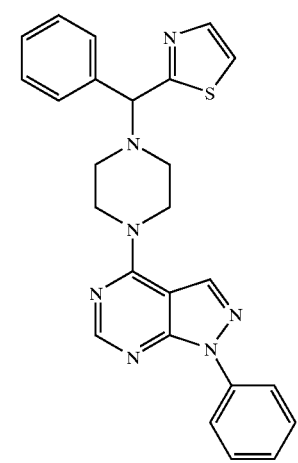
Compound 30
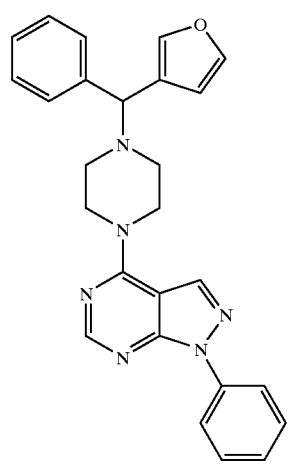
Compound 31
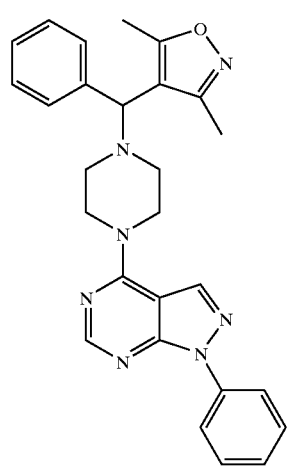
Compound 32
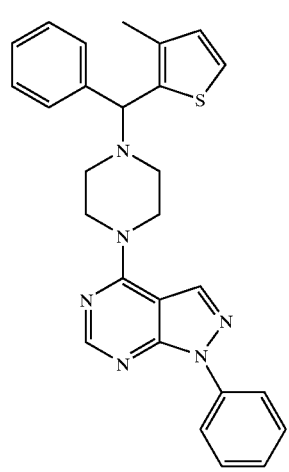

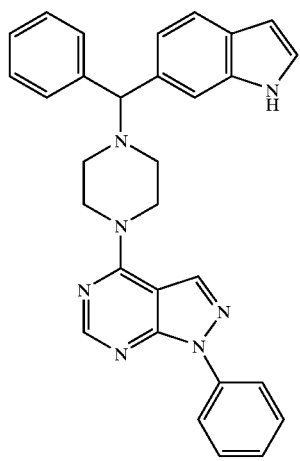
Compound 33
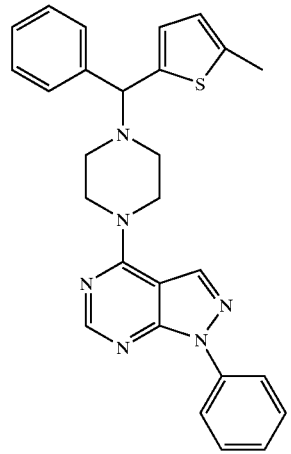
Compound 36
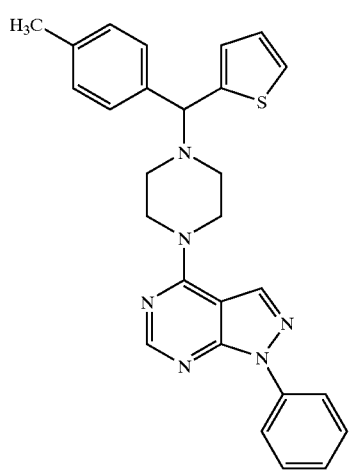
Compound 34
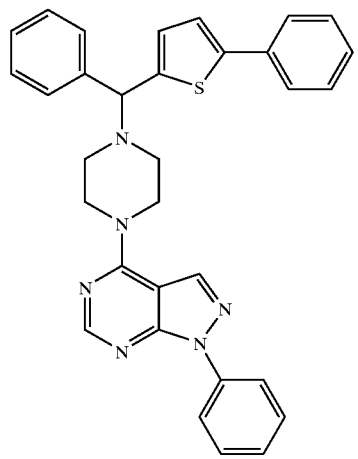
Compound 37
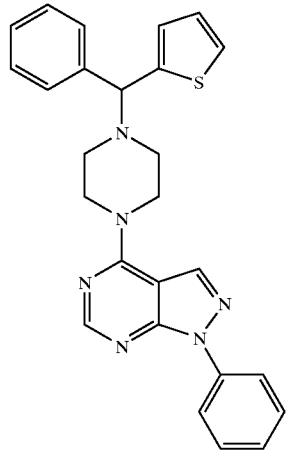
Compound 35
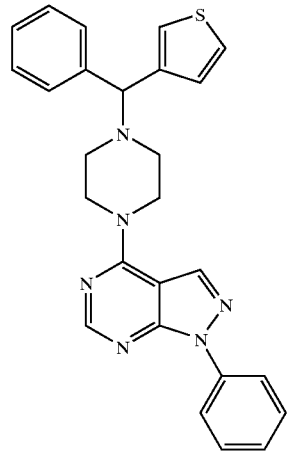
Compound 38

Compound 39

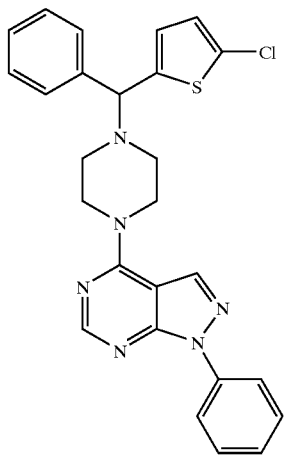

Compound 40

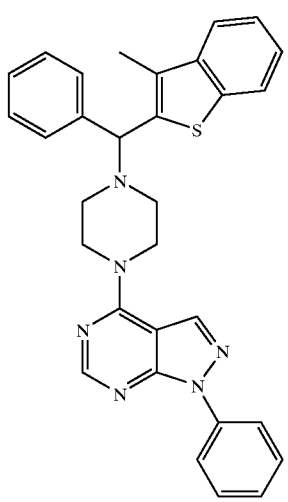

Compound 41

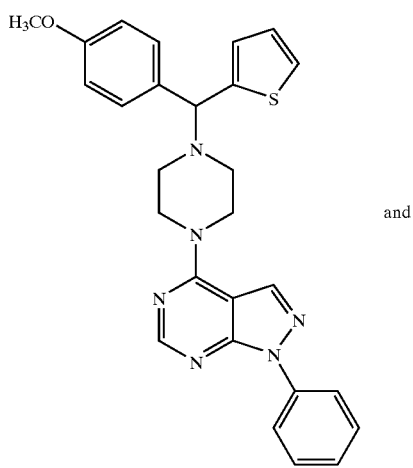

and

Compound 42

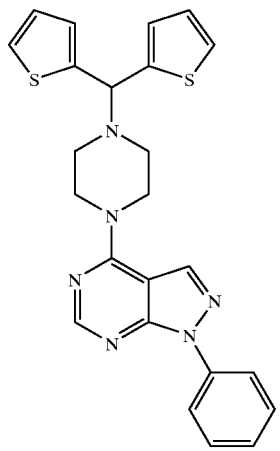

Other features, objects, and advantages of the invention will be apparent from the description and from the claims.

DETAILED DESCRIPTION

The pyrazolopyrimidine compounds described above can be prepared by methods well known in the art, as well as by the synthetic route disclosed herein. Shown below is a scheme that depicts an exemplary synthetic route. In this scheme, $R^a$, $R^b$, $R_1$, $R_2$, $R_3$, $R_4$, $R_5$, m, n, o, and p are as defined in Summary.

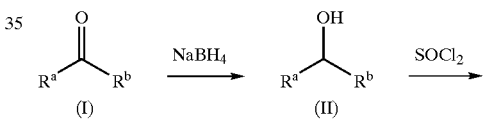

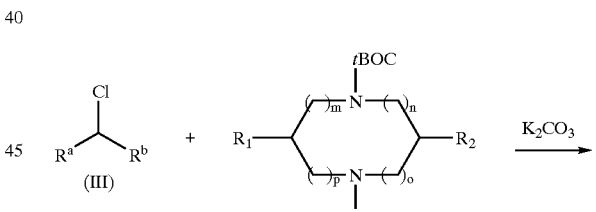

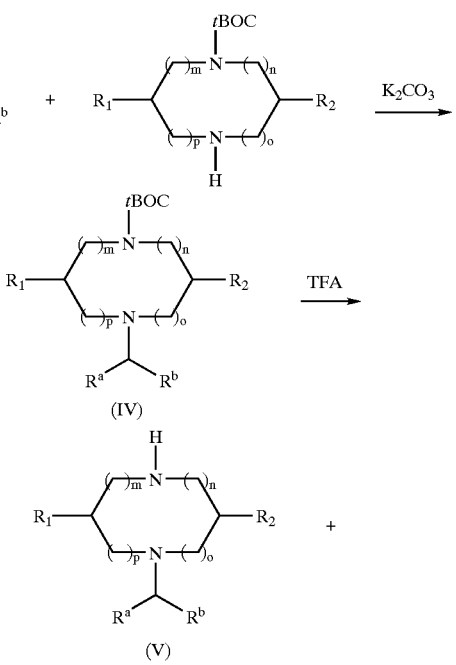

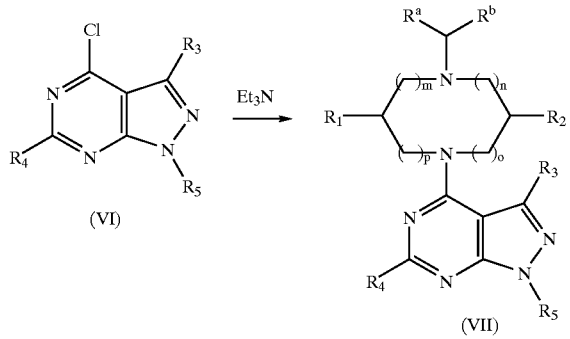

More specifically, a compound of formula (I) is reacted with sodium borohydride in an alcohol (e.g., methanol) to form a compound of formula (II), chlorination of which affords a compound of formula (III). A compound of formula (IV) is formed from a reaction between a compound (III) and a tert-butoxycarbonyl (tBOC) protected diamino compound. A desired compound (VII) is produced by deprotection of the tBOC group and a nucleophilic substitution reaction between compound (V) and a chloro-substituted compound (VI). One example of the chloro-substituted compound (VI) is 4-chloro-1-phenyl-1H-pyrazolo[3,4-d]pyrimidine (VI), which can be readily prepared by chlorination of 1-phenyl-1H-pyrazolo[3,4-d]pyrimidin-4-ol with phosphoryl chloride as described in, e.g., Davies et al. (1945) *J. Chem. Soc.* 347.

An alternative synthetic route is shown in the scheme below. Similarly, $R^a$, $R^b$, $R_1$, $R_2$, $R_3$, $R_4$, $R_5$, m, n, o, and p are as defined in Summary.

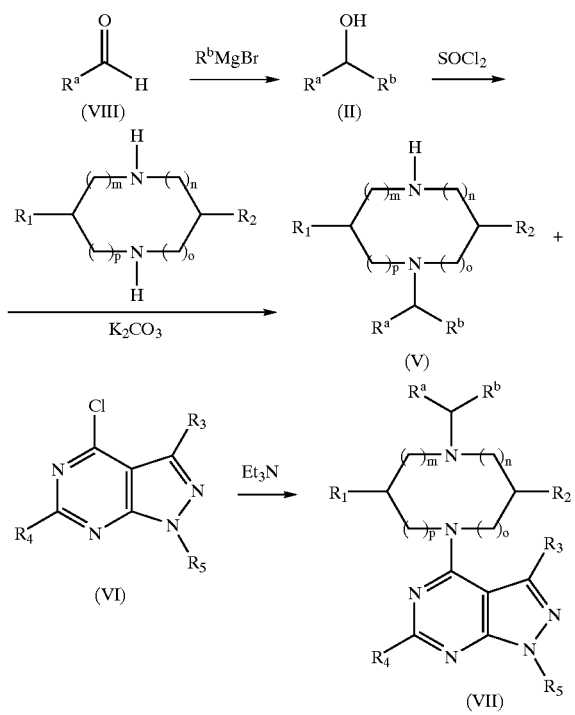

Compound (VIII) is reacted with a Grignard reagent to form compound (II). Compound (II) is then chlorinated and coupled with piperazine derivatives to afford compound (V). A nucleophilic substitution reaction between compounds (VI) and (V) affords a desired compound (VII) in quantitative yield.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the pyrazolopyrimidine compound. In addition, various synthetic steps may be performed in an alternate sequence or order to give the desired compounds. Synthetic chemistry transformations and protecting group methodologies (protection and deprotection) useful in synthesizing applicable pyrazolopyrimidine compounds are known in the art and include, for example, those described in R. Larock, *Comprehensive Organic Transformations*, VCH Publishers (1989); T. W. Greene and P.G.M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A pyrazolopyrimidine compound thus synthesized can be further purified by a method such as column chromatography, high pressure liquid chromatography, or recrystallization.

This invention features a method for treating infection by enteroviruses. The method includes administering to a subject in need thereof an effective amount of one or more pyrazolopyrimidine compounds and a pharmaceutically acceptable carrier. The term "treating" is defined as the application or administration of a composition including the pyrazolopyrimidine compound to a subject, who has an enteroviral infection, a symptom of the infection, a disease or disorder secondary to the infection, or a predisposition toward the infection, with the purpose to cure, alleviate, relieve, remedy, or ameliorate the infection, the symptom of the infection, the disease or disorder secondary to the infection, or the predisposition toward the infection. "An effective amount" is defined as the amount of a pyrazolopyrimidine compound which, upon administration to a subject in need thereof, is required to confer therapeutic effect on the subject. An effective amount of the pyrazolopyrimidine compound may range from 20 mg/Kg to 200 mg/Kg. Effective doses also vary, as recognized by those skilled in the art, depending on route of administration, excipient usage, and the possibility of co-usage with any other therapeutic agent, such as an antiviral agent.

To practice the method of the present invention, a pyrazolopyrimidine compound can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection, and infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with pyrazolopyrimidine compounds), can be utilized as pharmaceutical excipients for delivery of pyrazolopyrimidine compounds. Examples of other carriers include colloidal silicon dioxide, magnesium stearate, cellulose, sodium lauryl sulfate, and D&C Yellow # 10.

A pyrazolopyrimidine compound thus prepared can be preliminarily screened by an in vitro inhibition assay (e.g., plaque reduction assay) for its activity against enteroviruses. A compound that demonstrates high activity in the preliminary screening can be further evaluated by in vivo methods well known in the art (see, e.g., Daniel C. Pevear et al. (1999) *Antimicrobial Agents & Chemotherapy* 43(9): 2109–2115).

Without further elaboration, it is believed that the above description has adequately enabled the present invention. The following specific embodiment is, therefore, to be construed as merely illustrative, and not limitative of the remainder of the disclosure in any way whatsoever. All of the publications cited herein are hereby incorporated by reference in their entirety.

EXAMPLE 1

Synthesis of 4-(4-benzhydrylpiperazino)-1-phenyl-1H-pyrazolo[3,4-d]pyrimidine (Compound 1)

4-chloro-1-phenyl-1H-pyrazolo[3,4-d]pyrimidine was prepared by a route depicted in the following scheme, which was subsequently used as a common intermediate for the synthesis of pyrazolopyrimidine compounds of formula (A).

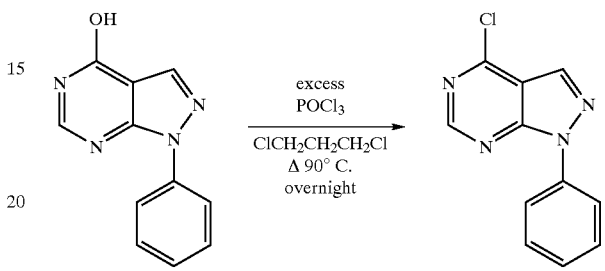

A solution of 4-chloro-1-phenyl-1H-pyrazolo[3,4-d]pyrimidine (230 mg, 1.00 mol), 1-(diphenylmethyl)piperazine (252 mg, 1.00 mol), and dry $Et_3N$ (30 mL) in ethyl alcohol (60 mL) was heated for 2 hr at 90° C. with stirring. The solvent was evaporated in vacuo, and the residue was partitioned between ethyl acetate and water. The organic layers were combined and washed with brine, dried over magnesium sulfate, and concentrated under reduced pressure. The crude mixture thus obtained was purified by silica gel chromatography [ethyl acetate and n-hexane (20:80)] to produce compound 1 as a white solid (423 mg, 95%). $^1$H-NMR ($CDCl_3$, ppm): 8.41 (s, 1H), 8.08 (d, 2H), 8.04 (s, 1H), 7.52–7.44 (m, 6H), 7.33–7.21 (m, 7H), 4.29 (brs, 1H), 4.01 (brs, 4H), 2.57 (brs, 4H). ESMS 447.3 (M+1).

EXAMPLES 2–42

Synthesis of Compounds 2–42

Each of the pyrazolopyrimidine compounds listed in the following table was prepared by the method described in Example 1. This table includes $^1$H Nuclear magnetic resonance (NMR) and mass spectroscopy data for compounds 2–42. The columns "Mass (Cald.)," "M+1," and "Mass+23" refer to the calculated mass, the measured mass, and the mass associated with $Na^+$, respectively.

| Example (Cpd ID) | Name | NMR (CDCl$_3$, ppm) | Mass (Cald.) | M+1 | Mass+23 |
|---|---|---|---|---|---|
| 2 | 4-4-[di(4-fluorophenyl)methyl]piperazino-1-phenyl-1H-pyrazolo[3,4-d]pyrimidine | 8.43 (s, 1H), 8.11 (d, 2H), 8.06 (s, 1H), 7.51 (t, 2H), 7.43-7.33 (m, 5H), 7.02 (t, 4H), 4.30 (brs, 1H), 4.03 (brs, 4H), 2.56 (brs, 4H) | 482.2 | 483.3 | |
| 3 | 4-4-[(4-chlorophenyl)(phenyl)methyl]piperazino-1-phenyl-1H-pyrazolo[3,4-d]pyrimidine | 8.43 (s, 1H), 8.11 (d, 2H), 8.06 (s, 1H), 7.51 (t, 2H), 7.43-7.28 (m, 10H), 4.29 (brs, 1H), 4.03 (brs, 4H), 2.58 (brs, 4H) | 480.2 | 481.1 | 503.3 (M+23) |
| 4 | 4-[4-(4-methoxybenzyl)piperazino]-1-phenyl-1H-pyrazolo[3,4-d]pyrimidine | 8.44 (s, 1H), 8.11 (d, 2H), 8.09 (s, 1H), 7.51 (t, 2H), 7.35-7.26 (m, 3H), 6.89 (d, 2H), 4.03 (t, 4H), 3.81 (s, 3H), 3.53 (s, 2H), 2.61 (t, 4H) | 400.2 | 401.2 | 423.3 (M+23) |

-continued

| Example (Cpd ID) | Name | NMR (CDCl$_3$, ppm) | Mass (Cald.) | M+1 | Mass+ 23 |
|---|---|---|---|---|---|
| 5 | 4-[4-(4-phenylbenzyl)piperazino]-1-phenyl-1H-pyrazolo[3,4-d]pyrimidine | 8.46 9s, 1H), 8.13-8.10 (m, 3H), 7.63-7.33 (m, 12H), 4.06 (t, 4H), 3.64 (s, 2H), 2.67 (t, 4H) | 446.2 | 447.3 | 469.2 (M+23) |
| 6 | 4-[4-(2-naphthylmethyl)piperazino]-1-phenyl-1H-pyrazolo[3,4-d]pyrimidine | 8.45 (s, 1H), 8.11 (d, 2H), 8.09 (s, 1H), 7.86-7.83 (m, 3H), 7.78 (s, 1H), 7.56-7.47 (m, 5H), 7.33 (t, 1H), 4.05 (t, 4H), 3.75 (s, 2H), 2.68 (t, 4H) | 420.2 | 421.3 | 443.2 (M+23) |
| 7 | 4-[4-(1,3-benzodioxol-5-ylmethyl)piperazino]-1-phenyl-1H-pyrazolo[3,4-d]pyrimidine | 8.42 (s, 1H), 8.09 (d, 2H), 8.07 (s, 1H), 7.49 (t, 2H), 7.31 (t, 1H), 6.88 (s, 1H), 6.75 (s, 2H), 5.94 (s, 2H), 4.01 (t, 4H), 3.48 (s, 2H), 2.59 (t, 4H) | 414.2 | 415.1 | |
| 8 | 4-[4-(9H-9-fluorenyl)piperazino]-1-phenyl-1H-pyrazolo[3,4-d]pyrimidine | 8.42 (s, 1H), 8.09 (d, 2H), 8.02 (s, 1H), 7.71 (d, 2H), 7.64 (d, 2H), 7.51 9t, 2H), 7.42-7.26 (m, 5H), 4.94 (s, 1H), 4.00 (brs, 4H), 2.81 (brs, 4H) | 444.2 | 445.2 | 467.1 (M+23) |
| 9 | 4-(4-benzylpiperazino)-1-phenyl-1H-pyrazolo[3,4-d]pyrimidine | 8.45 (s, 1H), 8.11 (d, 2H), 8.10 (s, 1H), 7.52 (t, 2H), 7.37-7.31 (m, 6H), 4.04 (t, 4H), 3.59 (s, 2H), 2.63 (t, 4H) | 370.2 | 371.2 | 393.1 (M+23) |
| 10 | 1-phenyl-4-[4-(3-thienylmethyl)piperazino]-1H-pyrazolo[3,4-d]pyrimidine | 8.43 (s, 1H), 8.10 (d, 2H), 8.09 (s, 1H), 7.50 (t, 2H), 7.31-7.29 (m, 2H), 7.15 (s, 1H), 7.09 (d, 1H), 4.02 (t, 4H), 3.60 (s, 2H), 2.61 (t, 4H) | 376.2 | 377.3 | |
| 11 | 4-4-[2-naphthyl(phenyl)methyl]piperazino-1-phenyl-1H-pyrazolo[3,4-d]pyrimidine | 8.44 (s. 1H), 8.11 (d, 2H), 8.05 (s, 1H), 7.89 (s, 1H), 7.82-7.79 (m, 3H), 7.66 (d, 1H) 7.56-7.44 (m, 6H), 7.35-7.22 (m, 4H), 4.48 (s, 1H), 4.05 (t, 4H), 2.65 (t, 4H) | 496.2 | 497.3 | |
| 12 | 4-(4-benzhydryl-1,4-diazepan-1-yl)-1-phenyl-1H-pyrazolo[3,4-d]pyrimidine | 8.45 (s, 1H), 8.13 (d, 2H), 8.10, 8.09 (s, 1H), 7.52 (t, 2H), 7.40-7.16 (m, 11H), 4.60 (s, 1H), 4.20-3.85 (m, 4H), 3.95 (s, 1H), 3.85 (s, 1H), 3.67 (s, 2H), 2.10 (s, 1H), 2.00 (s, 1H) | 460.2 | 461.4 | |
| 13 | N1-benzhydryl-N3-(1-phenyl-1H-pyrazolo[3,4-d]pyrimidin-4-yl)-1,3-propanediamine | | 458.2 | 459.2 | |
| 14 | 4-4-[(4-bromophenyl)(phenyl)methyl)piperazino-1-phenyl-1H-pyrazolo[3,4-d]pyrimidine | 8.43 (s, 1H), 8.11 (d, 2H), 8.06 (s, 1H), 7.54-7.24 (m, 12H), 4.27 (s, 1H), 4.02 (t, 4H), 2.58 (t, 4H) | 524.1 | 525.1 | |
| 15 | 1-phenyl-4-(4-phenyl[4-(trifluoromethyl)phenyl]methylpiperazino)-1H-pyrazolo[3,4-d]pyrimidine | 8.43 (s, 1H), 8.09 (dd, 2H), 8.06 (s, 1H), 7.64-7.25 (m, 12H), 4.38 (s, 1H), 4.05 (t, 4H), 2.60 (dd, 4H) | 514.2 | 515.2 | 537.2 (M+23) |
| 16 | 1-phenyl-4-(4-phenyl[4-biphenyl]methylpiperazino)-1H-pyrazolo[3,4-d]pyrimidine | 8.43 (s, 1H), 8.09 (d, 2H), 8.06 (s, 1H), 7.57-7.24 (m, 17H), 4.34 (s, 1H), 4.04 (t, 4H), 2.62 (t, 4H) | 522.3 | 523.3 | |
| 17 | 4-phenyl[4-(1-phenyl-1H-pyrazolo[3,4-d]pyrimidin-4-yl)piperazino]methylbenzonitrile | 8.43 (s, 1H), 8.09 (d, 2H), 8.06 (s, 1H), 7.62 (s, 4H), 7.52 (t, 2H), 7.42-7.28 (m, 6H), 4.37 (s, 1H), 4.05 (t, 4H), 2.59 (dd, 4H) | 471.2 | 472.2 | 494.2 (M+23) |
| 18 | 3-phenyl[4-(1-phenyl-1H-pyrazolo[3,4-d]pyrimidin-4-yl)piperazino]methylbenzonitrile | 8.43 (s, 1H), 8.19 (dd, 2H), 8.06 (s, 1H), 7.82 (s, 1H), 7.54-7.27 (m, 11H), 4.37 (s, 1H), 4.06 (brs, 4H), 2.59 (brs, 4H) | 471.2 | 472.2 | 494.2 (M+23) |
| 19 | 4-4-[(2-methylphenyl)(phenyl)methyl]piperazino-1-phenyl-1H-pyrazolo[3,4-d]pyrimidine | 8.43 (s, 1H), 8.10 (d, 2H), 8.05 (s, 1H), 7.87 (d, 2H), 7.53 (t, 1H), 7.49-7.08 (m, 9H), 4.50 (s, 1H), 4.01 (t, 4H), 2.68-2.47 (m, 4H), 2.35 (s, 3H) | 460.2 | 461.2 | |
| 20 | 4-4-[di(4-chlorophenyl)methyl]piperazino-1-phenyl-1H-pyrazolo[3,4-d]pyrimidine | 8.43 (s, 1H), 8.09 (d, 2H), 8.06 (s, 1H), 7.52 (t, 2H), 7.39-7.28 (m, 9H), 4.28 (s, 1H), 4.03 (t, 4H), 2.58 (t, 4H) | 514.1 | 515.1 | |

-continued

| Example (Cpd ID) | Name | NMR (CDCl$_3$, ppm) | Mass (Cald.) | M+1 | Mass+ 23 |
|---|---|---|---|---|---|
| 21 | N1,N1-diethyl-4-phenyl[4-(1-phenyl-1H-pyrazolo[3,4-d]pyrimidin-4-yl)piperazino]methylbenzamide | 8.43 (s, 1H), 8.09 (dd, 2H), 8.07 (s, 1H), 7.50 (dd, 4H), 7.44-7.22 (m, 8H), 4.32 (s, 1H), 4.03 (t, 4H), 3.53 (brs, 2H), 3.27 (brs, 2H), 2.60 (t, 4H), 1.26-1.13 (m, 6H) | 545.3 | 546.2 | 568.2 (M+23) |
| 22 | 1-phenyl-4-4-[phenyl(4-pyridyl)methyl]piperazino-1H-pyrazolo[3,4-d]pyrimidine | 8.54 (d, 2H), 8.42 (s, 1H), 8.08 (dd, 2H), 8.05 (s, 1H), 7.50 (t, 2H), 7.43-7.25 (m, 8H), 4.31 (s, 1H), 404 (t, 4H), 2.58 (t, 4H) | 447.2 | 448.2 | 470.2 (M+23) |
| 23 | 1-phenyl-4-4-[phenyl(3-pyridyl)methyl]piperazino-1H-pyrazolo[3,4-d]pyrimidine | 8.71 (s, 1H), 8.47 (d, 1H), 8.42 (s, 1H), 8.08 (d, 2H), 8.05 (s, 1H), 7.79 (d, 1H), 7.50 (t, 2H), 7.44-7.27 (m, 7H), 4.36 (s, 1H), 4.03 (brs, 4H), 2.60 (dd, 4H) | 447.2 | 448.2 | 470.2 (M+23) |
| 24 | 1-phenyl-4-4-[phenyl(2-pyridyl)methyl]piperazino-1H-pyazolo[3,4-d]pyrimidine | 8.54 (d, 1H), 8.41 (s, 1H), 8.08 (dd, 2H), 8.04 (s, 1H), 7.66-7.46 (m, 6H), 7.34-7.23 (m, 4H), 7.15 (t, 1H), 4.49 (s, 1H), 4.04 (t, 4H), 2.68-2.56 (m, 4H) | 447.2 | 448.2 | 470.2 (M+23) |
| 25 | 4-4-[1-naphthyl(phenyl)methyl]piperazino-1-phenyl-1H-pyrazolo[3,4-d]pyrimidine | 8.44 (s, 1H), 8.11 (d, 2H), 8.04 (s, 1H), 7.86-7.76 (m, 2H), 7.50-7.42 (m, 7H), 7.7.31-7.19 (m, 6H), 4.42 (s, 1H), 4.05 (brs, 4H), 2.71-2.62 (m, 4H) | 496.2 | 497.2 | 519.2 (M+23) |
| 26 | 1-phenyl-4-4-[phenyl(4-quinolyl)methyl]piperazino-1H-pyrazolo[3,4-d]pyrimidine | 8.97 (d, 1H), 8.42 (s, 1H), 8.30 (d, 1H), 8.11-8.10 (m, 3H), 8.1 (s, 1H), 8.08 (d, 1H), 7.66 (d, 2H), 7.63-7.46 (m, 4H), 7.33-7.20 (m, 4H), 5.09 (s, 1H), 4.04 (t, 4H), 2.68-2.58 (m, 4H) | 497.2 | 498.2 | 520.2 (M+23) |
| 27 | 1-phenyl-4-4-[phenyl(2-quinolyl)methyl]piperazino-1H-pyrazolo[3,4-d]pyrimidine | 8.42 (s, 1H), 8.16-8.04 (m, 5H), 7.80-7.61 (m, 5H), 7.49 (t, 3H), 7.35-7.22 (m, 4H), 4.73 (s, 1H), 4.05 (t, 4H), 2.79-2.58 (m, 4H) | 497.2 | 498.2 | 520.2 (M+23) |
| 28 | 1-phenyl-4-4-[phenyl(3-quinolyl)methyl]piperazino-1H-pyrazolo[3,4-d]pyrimidine | 9.07 (s, 1H), 8.41 (s, 1H), 8.17 (s, 1H), 8.07-8.04 (m, 3H), 7.79 (d, 1H), 7.68 (t, 1H), 7.55-7.47 (m, 5H), 7.36-7.25 (m, 5H), 4.55 (s, 1H), 4.06 (t, 4H), 2.65 (dd, 4H) | 497.2 | 498.2 | 520.2 (M+23) |
| 29 | 4-phenyl[4-(1-phenyl-1H-pyrazolo[3,4-d]pyrimidin-4-yl)piperazino]methyl-1,3-thiazole | 8.42 (s, 1H), 8.10-8.09 (m, 3H), 7.15 (d, 1H), 7.53-7.48 (m, 4H), 7.40-7.28 (m, 5H), 4.94 (s, 1H), 4.07 (t, 4H), 2.76-2.64 (m, 4H) | 453.2 | 454.2 | 476.2 (M+23) |
| 30 | 4-4-[3-furyl(phenyl)methyl]piperazino-1-phenyl-1H-pyrazolo[3,4-d]pyrimidine | 8.42 (s, 1H), 8.10 (d, 2H), 8.07 (s, 1H), 7.51 (t, 2H), 7.45-7.26 (m, 8H), 6.44 (s, 1H), 4.41 (s, 1H), 4.03 (t, 4H), 2.61 (dd, 4H) | 436.2 | 437.2 | 459.2 (M+23) |
| 31 | 3,5-dimethyl-4-phenyl[4-(1-phenyl-1H-pyrazolo[3,4-d]pyrimidin-4-yl)piperazino]methylisoxazole | 8.45 (d, 1H), 8.12 (d, 2H), 8.08 (s, 1H), 7.52 (t, 2H), 7.40-7.25 (m, 6H), 4.24 (s, 1H), 4.09-4.00 (m, 4H), 3.02-2.98 (m, 4H), 2.59 (s, 3H), 2.29 (s, 3H) | 465.2 | 466.2 | 488.2 (M+23) |
| 32 | 4-4-[(3-methyl-2-thienyl)(phenyl)methyl]piperazino-1-phenyl-1H-pyrazolo[3,4-d]pyrimidine | 8.43 (s, 1H), 8.11 (dd, 2H), 8.06 (s, 1H), 7.48-7.54 (m, 4H), 7.26-7.37 (m, 4H) 7.16 (d, 1H), 6.72 (d, 1H), 4.63 (s, 1H), 4.03 (t, 4H), 2.58-2.71 (m, 4H), 2.24 (s, 3H) | 466.2 | 467.2 | |
| 33 | 4-4-[1H-6-indolyl(phenyl)methyl]piperazino-1-phenyl-1H-pyrazolo[3,4-d]pyrimidine | 8.41 (s, 1H), 8.16 (brs, 1H), 3.08 (d, 2H), 8.03 (s, 1H), 7.57-7.47 (m, 6H), 7.33-7.15 (m, 6H), 6.49 (s, 1H), 4.38 (s, 1H), 4.02 (brs, 4H), 2.62 (brs, 4H) | 485.2 | 486.2 | 508.2 (M+23) |
| 34 | 4-4-[(4-methylphenyl)(2-thienyl)methyl]piperazino-1-phenyl-1H-pyrazolo[3,4-d]pyrimidine | 8.41 (s, 1H), 8.10 (d, 2H), 8.06 (s, 1H), 7.51 (t, 2H), 7.36-7.15 (m, 6H), 6.93-6.91 (m, 2H), 4.69 (s, 1H), 4.03 (t, 4H), 2.63 (brs, 4H), 2.34 (s, 3H) | 466.2 | 467.2 | 489.2 (M+23) |
| 35 | 1-phenyl-4-4-[phenyl(2-thienyl)methyl]piperazino-1H-pyrazolo[3,4-d]pyrimidine | 8.42 (s, 1H), 8.09 (dd, 2H), 8.06 (s, 1H), 7.54-7.46 (m, 4H), 7.39-7.30 (m, 4H), 7.26 (m, 1H), 6.95-6.91 (m, 2H), 4.72 (s, 1H), 4.04 (t, 4H), 2.64 (t, 4H) | 452.2 | 453.2 | |
| 36 | 4-4-[(5-methyl-2-thienyl)(phenyl)methyl]piperazino-1-phenyl-1H-pyrazolo[3,4-d]pyrimidine | 8.42 (s, 1H), 8.09 (dd, 2H), 8.06 (s, 1H), 7.53-7.46 (m, 4H), 7.37-7.25 (m, 4H), 6.73 (d, 1H), 6.54 (m, 1H), 4.58 (s, 1H), 4.03 (t, 4H), 2.63 (t, 4H), 2.44 (s, 3H) | 466.2 | 467.2 | |

-continued

| Example (Cpd ID) | Name | NMR (CDCl$_3$, ppm) | Mass (Cald.) | M+1 | Mass+ 23 |
|---|---|---|---|---|---|
| 37 | 1-phenyl-4-4-[phenyl(5-phenyl-2-thienyl)methyl]piperazino-1H-pyrazolo[3,4-d]pyrimidine | 8.42 (s, 1H), 8.08 (dd, 2H), 8.07 (s, 1H), 7.58-7.48 (m, 6H), 7.40-7.26 (m, 7H), 7.12 (d, 1H), 6.91 (d, 1H), 4.69 (s, 1H), 4.06 (t, 4H), 2.68 (t, 4H) | 528.2 | 529.2 | 551.2 (M+23) |
| 38 | 1-phenyl-4-4-[phenyl(3-thienyl)methyl]piperazino-1H-pyrazolo[3,4-d]pyrimidine | 8.42 (s, 1H), 8.09 (d, 2H), 8.06 (s, 1H), 7.53-7.44 (m, 4H), 7.36-7.26 (m, 5H), 7.21 (brs, 1H), 7.13 (d, 1H), 4.50 (s, 1H), 4.02 (t, 4H), 2.59 (t, 4H) | 452.2 | 453.2 | |
| 39 | 4-4-[(5-chloro-2-thienyl)(phenyl)methyl]piperazino-1-phenyl-1H-pyrazolo[3,4-d]pyrimidine | 8.40 (s, 1H), 8.07 (d, 2H), 8.04 (s, 1H), 7.49 (t, 2H), 7.41-7.28 (m, 6H), 6.68 (dd, 2H), 4.61 (s 1H), 4.02 (t, 4H), 2.62 (t, 4H) | 486.1 | 487.1 | 509.1 (M+23) |
| 40 | 4-4-[(3-methylbenzo[b]thiophen-2-yl)(phenyl)methyl]piperazino-1-phenyl-1H-pyrazolo[3,4-d]pyrimidine | 8.42 (s, 1H), 8.08 (d, 2H), 8.04 (s, 1H), 7.75 (d, 1H), 7.61-7.47 (m, 5H), 7.33-7.24 (m, 6H), 4.79 (s, 1H), 4.04 (brs, 4H), 2.76-2.62 (m, 4H), 2.42 (s, 3H) | 516.2 | 517.2 | 539.1 (M+23) |
| 41 | 4-4-[(4-methoxyphenyl)(2-thienyl)methyl]piperazino-1-phenyl-1H-pyrazolo[3,4-d]pyrimidine | 8.39 (s, 1H), 8.07 (dd, 2H), 8.04 (s, 1H), 7.51-746 (m, 2H), 7.37-7.22 (m, 4H), 6.91-6.85 (m, 4H), 4.67 (s, 1H), 4.01 (t, 4H), 3.78 (s, 3H), 2.61 (t, 4H) | 482.2 | 483.2 | 505.2 (M+23) |
| 42 | 4-[4-(di2-thienylmethyl)piperazino]-1-phenyl-1H-pyrazolo[3,4-d]pyrimidine | 8.39 (s, 1H), 8.07 (d, 2H), 8.05 (s, 1H), 7.51-7.46 (t, 2H), 7.33-7.27 (m, 3H), 6.99-6.94 (m, 4H), 5.20 (s, 1H), 4.05 (t, 4H), 2.68 (t, 4H) | 458.1 | 459.1 | 481.1 (M+23) |

EXAMPLE 43

Antiviral Activity Assay of Pyrazolopyrimidine Compounds 5 of the 42 pyrazolopyrimidine compounds thus prepared were tested for their antiviral activities, following a standard plaque reduction assay as described in Otto et al. (1985) *Antimicrobial Agents & Chemotherapy* 27:883–886.

The 5 compounds were tested against human enteroviruses, i.e., EV serotypes (EV68, EV71-2086, EV71-2231, EV71-BrCr, and EV71-1743), coxackievirus serotypes (COX-A9, -A10, -A16, -A24, -B1, -B2, -B3, -B4, -B5, and -B6), and echovirus serotypes (-9 and -29). Further, those compounds were also tested against non-enrteroviruses, i.e., human rhinovirus-2 and -14, human herpes simplex virus 1, influenza A, and influenza B.

EV68, EV71-1743, EV71-2086, EV71-2231, COX-A9, -A10, -A16, -A24, COX-B1, -B2, -B3, -B4, -B5, -B6, echovirus-9 and -29, and herpes simplex virus 1 isolates were obtained from Chang Gung Children's Hospitals (Taipei, Taiwan). EV71-2086 was isolated from the skin lesion of a HFMD (hand, foot, and mouth disease) patient. EV71-2231 was isolated from throat swabs of a patient. EV71-BrCr, a prototype of EV71, was obtained from the American Type Culture Collection (ATCC Accession No. VR 784). Rhinovirus-2 and -14, influenza A, and influenza B were obtained from the American Type Culture Collection with ATCC Accession Nos. VR-482, VR-284, VR-825, and VR-823, respectively. MRC-5 cells (ATCC Accession No. CCL-171) and Vero cells (ATCC Accession No. CCL-81) were used for virus isolation and propagation.

Monolayers of vero cells on the top of agar in agar plates were infected by virus at a concentration of approximately 50–100 pfu (plaque forming unit) per plate. A test compound was serially diluted and added to the monolayers. The plates were then incubated at 35° C. for 96 hr. The plaques were stained with crystal violet and counted, and the IC$_{50}$ value of each test compound was determined. IC$_{50}$ is the concentration at which a compound reduces the number of plaques by 50% as compared with an untreated control.

Unexpectedly, all 5 pyrazolopyrimidine compounds showed antiviral activity against all enteroviruses (IC$_{50}$ values less than 1 $\mu$M and as low as 0.085 $\mu$M), in particular, against COX-A24, -B2, -B3, or -B4. In contrast, these compounds showed little efficacy against the non-enteroviruses (IC$_{50}$ values higher than 25 $\mu$M).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of formula (A):

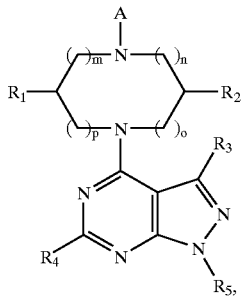

(A)

wherein

A is $(CH_2)_q—CHR^aR^b$;

each of $R_1$ and $R_2$, independently, is hydrogen, halogen, cyano, nitro, or alkyl; or $R_1$ and $R_2$ taken together is $(CH_2)_r$;

each of $R_3$ and $R_4$, independently, is hydrogen, halogen, cyano, nitro, or alkyl;

each of $R_5$, $R^a$, and $R^b$, independently, is aryl, aralkyl, or a 5–6 membered aromatic ring, optionally fused, containing 1–3 heteroatoms selected from the group consisting of O, N, and S, optionally substituted with halogen, cyano, nitro, alkyl, aryl, aralkyl, a 5–6 membered aromatic ring, optionally fused, containing 1–3 heteroatoms selected from the group consisting of O, N, and S, OR, O(O)CR, C(O)R, C(O)OR, C(O)NRR', SR, S(O)R, S(O)OR, NRR', NR(O)CR', NRC(O)OR', or NRC(O)NR'R";

each of m, n, o, p, and r, independently, is 0 or 1, and q is 0, 1, or 2;

in which each of R, R', and R", independently, is hydrogen or alkyl, provided that the sum of m, n, o, and p is 1, 2, 3, or 4.

2. The compound of claim 1, wherein q is 0, and each of $R^a$ and $R^b$, independently, is aryl.

3. The compound of claim 1, wherein $R_5$ is aryl.

4. The compound of claim 3, wherein $R_5$ is phenyl.

5. The compound of claim 1, wherein each of $R_1$ and $R_2$, independently, is hydrogen.

6. The compound of claim 5, wherein the sum of m and p is 1, and the sum of n and o is 1.

7. The compound of claim 6, wherein q is 0, and each of $R^a$ and $R^b$, independently, is aryl or a 5–6 membered aromatic ring, optionally fused, containing 1–3 heteroatoms selected from the group consisting of O, N, and S.

8. The compound of claim 7, wherein $R_5$ is phenyl.

9. The compound of claim 8, wherein each of $R_3$ and $R_4$ is hydrogen.

10. The compound of claim 9, wherein each of $R^a$ and $R^b$ is phenyl or each of $R^a$ and $R^b$ is 2-thienyl.

11. The compound of claim 9, wherein one of $R^a$ and $R^b$ is phenyl, and the other is naphthyl, pyridyl, quinolyl, thiazolyl, furyl, thienyl, indolyl, 3,5-dimethyl-2-ixocazole, 3-methyl-2-thienyl, or 3-methyl-2-benzo[b]thienyl.

12. The compound of claim 5, wherein the sum of m and p is 1, and the sum of n and o is 2.

13. The compound of claim 12, wherein q is 0, and each of $R^a$ and $R^b$, independently, is aryl.

14. The compound of claim 13, wherein $R_5$ is phenyl.

15. The compound of claim 14, wherein each of $R_3$ and $R_4$ is hydrogen.

16. The compound of claim 15, wherein each of $R^a$ and $R^b$ is phenyl.

17. The compound of claim 1, wherein $R_1$ and $R_2$ taken together is $(CH_2)_r$, and r is 1.

18. The compound of claim 17, wherein the sum of m and p is 1, and the sum of n and o is 1.

19. The compound of claim 18, wherein q is 0, and each of $R^a$ and $R^b$, independently, is aryl.

20. The compound of claim 19, wherein $R_5$ is phenyl.

21. The compound of claim 20, wherein each of $R_3$ and $R_4$ is hydrogen.

22. The compound of claim 21, wherein each of $R^a$ and $R^b$ is phenyl.

23. A compound of formula (A):

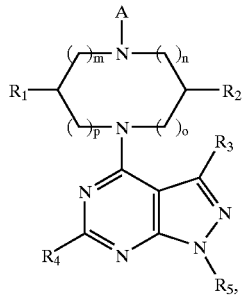

(A)

wherein

A is $(CH_2)_q—R^a$;

each of $R_1$ and $R_2$, independently is hydrogen, halogen, cyano, nitro, or alkyl; or $R_1$ and $R_2$ taken together is $(CH_2)_r$;

each of $R_3$ and $R_4$, independently, is hydrogen, halogen, cyano, nitro, or alkyl;

$R_5$ is aryl, aralkyl, or a 5–6 membered aromatic ring, optionally fused, containing 1–3 heteroatoms selected from the group consisting of O, N, and S, optionally substituted with halogen, cyano, nitro, alkyl, aryl, aralkyl, a 5–6 membered aromatic ring, optionally fused, containing 1–3 heteroatoms selected from the group consisting of O, N, and S, OR, O(O)CR, C(O)R, C(O)OR, C(O)NRR', SR, S(O)R, S(O)OR, NRR', NR(O)CR', NRC(O)OR', or NRC(O)NR'R";

$R^a$ is aryl, aralkyl, or a 5–6 membered aromatic ring, optionally fused, containing 1–3 heteroatoms selected from the group consisting of O, N, and S, optionally substituted with halogen, cyano, nitro, alkyl, aryl, aralkyl, a 5–6 membered aromatic ring, optionally fused, containing 1–3 heteroatoms selected from the group consisting of O, N, and S, OR, O(O)CR, C(O)R, C(O)OR, C(O)NRR', SR, S(O)R, S(O)OR, NRR', NR(O)CR', NRC(O)OR', or NRC(O)NR'R";

each of m, n, o, p, and r, independently, is 0 or 1; and q is 1;

in which each of R, R', and R", independently, is hydrogen or alkyl, provided that the sum of m, n, o, and p is 1, 2, 3, or 4.

24. The compound of claim 23, wherein $R^a$ is a 5–6 membered aromatic ring, optionally fused, containing 1–3 heteroatoms selected from the group consisting of O, N, and S.

25. The compound of claim 23, wherein $R_5$ is aryl.

26. The compound of claim 25, wherein $R_5$ is phenyl.

27. The compound of claim 23, wherein each of $R_1$ and $R_2$ is hydrogen.

28. The compound of claim 27, wherein the sum of m and p is 1, and the sum of n and o is 1.

29. The compound of claim 28, wherein $R_5$ is phenyl.

30. The compound of claim 29, wherein each of $R_3$ and $R_4$ is hydrogen.

31. The compound of claim 30, wherein $R^a$ is thienyl.

32. A compound of formula (A):

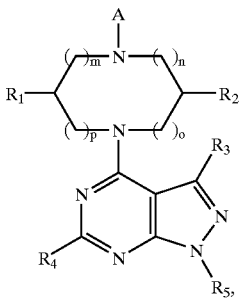

wherein

A is $(CH_2)_q-R^a$;

each of $R_1$ and $R_2$, independently is hydrogen, halogen, cyano, nitro, or alkyl; or $R_1$ and $R_2$ taken together is $(CH_2)_r$;

each of $R_3$ and $R_4$, independently, is hydrogen, halogen, cyano, nitro, or alkyl;

each of $R_5$ and $R^2$, independently, is aryl, aralkyl, or a 5–6 membered aromatic ring, optionally fused, containing 1–3 heteroatoms selected from the group consisting of O, N, and S, optionally substituted with halogen, cyano, nitro, alkyl, aryl, aralkyl, a 5–6 membered aromatic ring, optionally fused, containing 1–3 heteroatoms selected from the group consisting of O, N, and S, OR, O(O)CR, C(O)R, C(O)OR, C(O)NRR', SR, S(O)R, S(O)OR, NRR', NR(O)CR', NRC(O)OR', or NRC(O)NR'R";

each of m, n, o, p, and r, independently, is 0 or 1; and q is 0 or 2;

in which each of R, R', and R", independently, is hydrogen or alkyl, provided that the sum of m, n, o, and p is 1, 2, 3, or 4.

33. The compound of claim 32, wherein q is 0, and $R^a$ is aralkyl.

34. The compound of claim 32, wherein $R_5$ is aryl.

35. The compound of claim 34, wherein $R_5$ is phenyl.

36. The compound of claim 32, wherein each of $R_1$ and $R_2$ is hydrogen.

37. The compound of claim 36, wherein the sum of m and p is 1, and the sum of n and o is 1.

38. The compound of claim 37, wherein q is 0, and $R^a$ is aralkyl.

39. The compound of claim 38, wherein $R_5$ is phenyl.

40. The compound of claim 39, wherein each of $R_3$ and $R_4$ is hydrogen.

41. The compound of claim 40, wherein $R^a$ is fluorenyl.

* * * * *